US00PP17472P2

(12) United States Plant Patent
Hofman et al.

(10) Patent No.: US PP17,472 P2
(45) Date of Patent: Mar. 6, 2007

(54) *NEMESIA* PLANT NAMED 'INUPPINK'

(50) Latin Name: ***Nemesia* hybrid**
Varietal Denomination: Inuppink

(75) Inventors: Silvia Hofman, Mainz (DE); Hendrik Theobald, Heidesheim (DE)

(73) Assignee: Innovaplant GmbH + Co KG, Gensurgen (DE)

( * ) Notice: Subject to any disclaimer, the term of this patent is extended or adjusted under 35 U.S.C. 154(b) by 9 days.

(21) Appl. No.: 11/174,963

(22) Filed: Jul. 5, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

UPOV ROM GTITM Computer Database, GTI Jouve Retrieval Software 2006/05 Citations for 'Inuppink'.*

Sunsatia Blackberry, 'Innupink' available at http://www.pac–elsner.com/uk/beet–und–balkon/beet–und–balkon–nemesia.html.*

* cited by examiner

*Primary Examiner*—Wendy Haas
(74) *Attorney, Agent, or Firm*—C. A. Whealy

(57) ABSTRACT

A new and distinct cultivar of *Nemesia* plant named 'Inuppink', characterized by its upright and somewhat outwardly spreading plant habit; freely branching habit; dense and bushy appearance; early flowering habit; numerous large red purple-colored flowers; and long flowering period.

1 Drawing Sheet

Botanical designation: *Nemesia* hybrid.
Cultivar denomination: 'Inuppink'.

BACKGROUND OF THE INVENTION

The present invention relates to a new and distinct cultivar of *Nemesia* plant, botanically known as *Nemesia* hybrid and referred to by the name 'Inuppink'.

The new *Nemesia* is a product of a planned breeding program conducted by the Inventors in Gensingen, Germany. The objective of the program is to create new strong *Nemesia* cultivars with numerous flowers and unique flower colors.

The new *Nemesia* originated from a cross-pollination made by the Inventors of an unnamed *Nemesia fructicans* selection, not patented, as the female, or seed, parent with an unnamed *Nemesia strumosa* selection, not patented during the summer of 2001. The cultivar Inuppink was discovered and selected by the Inventors as a single flowering plant within the progeny of the stated cross-pollination in a controlled environment in Gensingen, Germany during the summer of 2002.

Asexual reproduction of the new *Nemesia* by terminal cuttings in a controlled environment in Gensingen, Germany since June, 2002, has shown that the unique features of this new *Nemesia* are stable and are reproduced true to type in successive generations.

SUMMARY OF THE INVENTION

The new *Nemesia* has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Inuppink' and distinguish 'Inuppink' as a new and distinct cultivar:

1. Upright to somewhat outwardly spreading plant habit.
2. Freely branching habit; dense and bushy appearance.
3. Early flowering habit.
4. Numerous large red purple-colored flowers.
5. Long flowering period.

Plants of the new *Nemesia* differ primarily from plants of the female parent selection in the following characteristics:

1. Plants of the new *Nemesia* have larger flowers than plants of the female parent selection.
2. Plants of the new *Nemesia* and the female parent selection differ in flower color as plants of the female parent selection have white to soft pink-colored flowers.

Plants of the new *Nemesia* differ primarily from plants of the male parent selection in the following characteristics:

1. Plants to the new *Nemesia* are more vigorous than plants of the male parent selection.
2. Plants of the new *Nemesia* flower for a longer period of time than plants of the male parent selection.

Plants of the new *Nemesia* can be compared to plants of the cultivar Inupcream, disclosed in U.S. Plant patent application Ser. No. 11/174,962. In side-by-side comparisons conducted in Gensingen, Germany, plants of the new *Nemesia* differed primarily from plants of the cultivar Inupcream in flower color as plants of the cultivar Inupcream had light yellow and white-colored flowers.

BRIEF DESCRIPTION OF THE PHOTOGRAPHS

The accompanying colored photographs illustrate the overall appearance of the new *Nemesia,* showing the colors as true as it is reasonably possible to obtain in colored reproductions of this type. Colors in the photographs may differ slightly from the color values cited in the detailed botanical description which accurately describe the colors of the new *Nemesia*.

The photograph at the bottom of the sheet comprises a side perspective view of a typical plant of 'Inuppink' grown in a container.

The photograph at the top of the sheet comprises a close-up view of typical flowers of 'Inuppink'.

DETAILED BOTANICAL DESCRIPTION

The aforementioned photographs and following observations and averaged measurements describe plants grown in Bonsall, Calif., in an outdoor nursery during the spring with day temperatures ranging from 18° C. to 35° C. and night temperatures ranging from 15° C. to 21° C. After rooting, plants were grown for ten weeks in 15-cm containers with one plant per container. Color references are made to The Royal Horticultural Society Colour Chart, 1995 Edition, except where general terms of ordinary dictionary significance are used.

Botanical classification: *Nemesia* hybrid cultivar Inuppink.

Parentage:

*Female parent.*—Unnamed *Nemesia fructicans* selection, not patented.

*Male parent.*—Unnamed *Nemesia strumosa* selection, not patented.

Propagation:

*Type.*—By vegetative cuttings.

*Time to initiate roots.*—About 10 to 14 days at 20° C.

*Time to develop roots.*—About two to three weeks at 20° C.

*Root description.*—Fine; white in color.

*Rooting habit.*—Freely branching.

Plant description:

*General appearance.*—Upright to somewhat outwardly spreading; inverted triangle. Freely branching, typically about twelve primary lateral branches; numerous secondary and tertiary lateral branches. Vigorous growth habit.

*Plant height.*—About 30 cm.

*Plant diameter or spread.*—About 40 cm.

*Lateral branches.*—Appearance: Square in cross-section with longitudinal ridges. Length: About 27 cm. Diameter: About 4 mm. Internode length: About 3.5 cm. Strength: Strong. Texture: Smooth, glabrous. Color: 144A.

*Foliage description.*—Arrangement: Opposite, simple. Shape: Lanceolate. Apex: Broadly acute. Base: Attenuate; clasping. Length: About 6 cm. Width: About 2.4 cm. Margin: Serrate. Texture, upper and lower surfaces: Smooth, glabrous. Venation pattern: Pinnate, arcuate. Petiole length: About 8 mm. Petiole diameter: About 4 mm. Petiole texture, upper and lower surfaces: Smooth, glabrous. Color: Developing leaves, upper surface: 147A. Developing leaves, lower surface: 147B. Fully expanded leaves, upper surface: 137A. Fully expanded leaves, lower surface: 147B. Venation, upper and lower surfaces: 147B. Petiole, upper and lower surfaces: 144A.

Flowering description:

*Arrangement/appearance.*—Zygomorphic solitary flowers arranged on terminal racemes; flowering acropetally towards apex. Flowers bilabiate with nectar spur. Flowers face upright and outward. Flowers last about five to seven days on the plant. Flowers not persistent.

*Natural flowering season.*—Long flowering period; natural flowering season is spring to fall; flowering continuous during this period.

*Quantity of flowers.*—Freely flowering with about ten open flowers per inflorescence.

*Fragrance.*—None detected.

*Inflorescence length.*—About 5 cm.

*Inflorescence diameter.*—About 6.3 cm.

*Flower diameter.*—About 2.7 cm by 2.5 cm.

*Flower depth, including nectar spur.*—About 1.7 cm.

*Flower buds.*—Shape: Ovoid with spur. Length including spur: About 1 cm. Diameter: About 6 mm. Color: 72A to 72B.

*Petals.*—Arrangement/shape: Five petals in a single whorl. Four upper petals are fused at base to form an upright lobed and arched banner lip; lower petal modified into a larger lip with nectar spur and central protuberance which serves as pollinator nectar guide and landing platform. Apex: Rounded. Margin: Entire. Length: Upper lip petals; About 1.2 to 1.4 cm. Lower lip petal: About 1.5 cm. Width: Upper lip petals: About 1 cm. Lower lip petal: About 2 cm. Texture, upper and lower surfaces: Smooth, velvety. Color: When opening, upper surface: 67A. When opening, lower surface: 61B. Fully opened, upper surface: 67A; towards the base, 17A; stripes at base, 79C; color becoming closer to 63A to 63B with development. Fully opened, lower surface: 61B. Nectar guide: 33A. Nectar spur: 61B.

*Sepals.*—Quantity: Five-parted, star-shaped calyx. Shape: Elliptic. Apex: Acute. Base: Fused. Margin: Entire. Length: About 5 mm. Diameter: About 2.5 mm. Texture, upper and lower surfaces: Pubescent. Color, upper and lower surfaces: 146A.

*Peduncle.*—Length: About 6 cm. Diameter: About 4 mm. Strength: Strong. Angle: Mostly upright. Color: 137A.

*Pedicel.*—Length: About 1.5 cm. Diameter: About 1.5 mm. Strength: Strong. Angle: About 45° to 60° from the stem. Color: 146B.

*Androecium.*—Stamen number: Four per flower. Anther shape: Oval. Anther length: Less than 1 mm. Anther color: 14A. Amount of pollen: Scarce. Pollen color: 14A.

*Gynoecium.*—Pistil number: One per flower. Pistil length: About 3 mm. Style length: About 1 mm. Style color: 145D. Stigma shape: Rounded. Stigma color: 145B. Ovary color: 144A.

*Seed/fruit.*—Seed and fruit production has not been observed on plants of the new *Nemesia*.

Disease/pest resistance: Plants of the new *Nemesia* have not been observed to be resistant to pathogens or pests common to *Nemesias*.

Temperature tolerance: Plants of the new *Nemesia* have been observed to be tolerant to temperatures ranging from 2° C. to 35° C.

It is claimed:

1. A new and distinct cultivar of *Nemesia* plant named 'Inuppink', as illustrated and described.

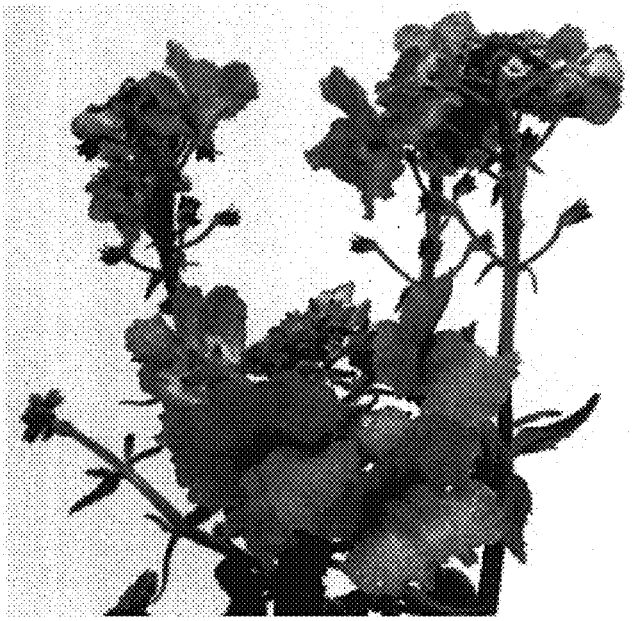
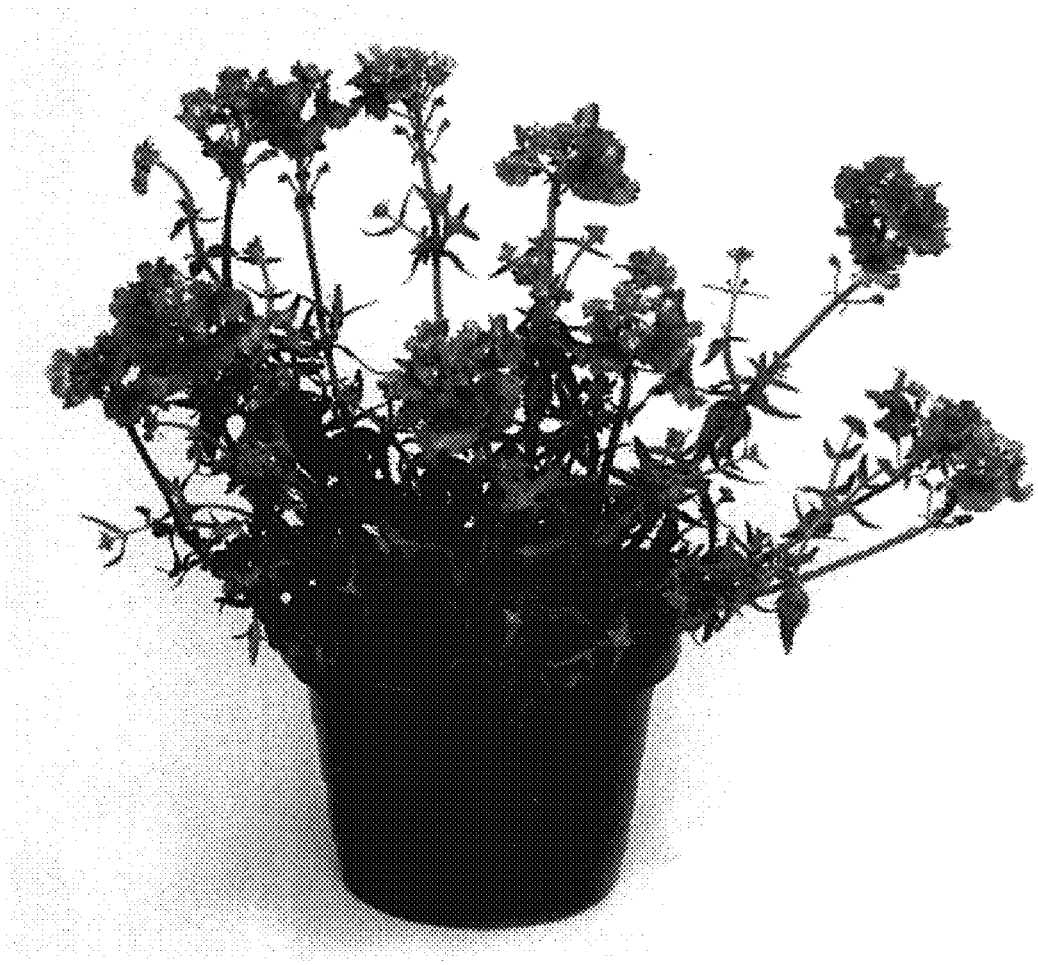

* * * * *